(12) United States Patent
Beller

(10) Patent No.: US 11,110,233 B2
(45) Date of Patent: Sep. 7, 2021

(54) SINGLE-DOSE POWDER INHALATOR AND METHOD FOR THE PRODUCTION THEREOF

(71) Applicants: Perlen Converting AG, Perlen (CH); Klaus-Dieter Beller, Kenzingen (DE)

(72) Inventor: Klaus-Dieter Beller, Kenzingen (DE)

(73) Assignee: Perlen Packaging AG, Perlen (CH)

( * ) Notice: Subject to any disclaimer, the term of this patent is extended or adjusted under 35 U.S.C. 154(b) by 562 days.

(21) Appl. No.: 15/529,264

(22) PCT Filed: Jul. 29, 2015

(86) PCT No.: PCT/EP2015/001558
§ 371 (c)(1),
(2) Date: May 24, 2017

(87) PCT Pub. No.: WO2016/082900
PCT Pub. Date: Jun. 2, 2016

(65) Prior Publication Data
US 2017/0312458 A1 Nov. 2, 2017

(30) Foreign Application Priority Data
Nov. 26, 2014 (DE) ..................... 10 2014 017 409.3

(51) Int. Cl.
*A61M 15/00* (2006.01)
(52) U.S. Cl.
CPC .... *A61M 15/0008* (2014.02); *A61M 15/0028* (2013.01); *A61M 2202/064* (2013.01); *A61M 2206/14* (2013.01)

(58) Field of Classification Search
CPC ...... A61M 11/00; A61M 11/02; A61M 13/00; A61M 15/00; A61M 15/0001;
(Continued)

(56) References Cited

U.S. PATENT DOCUMENTS 4,240,418 A 12/1980 Rosskamp et al.
5,239,991 A * 8/1993 Chawla ................. A61M 15/00
128/203.12
(Continued)

FOREIGN PATENT DOCUMENTS

CN 101815552 8/2010
CN 201692450 1/2011
(Continued)

*Primary Examiner* — Justine R Yu
*Assistant Examiner* — Matthew D Ziegler
(74) *Attorney, Agent, or Firm* — Gudrun E. Huckett

(57) ABSTRACT

The present invention provides a single-dose powder inhalator and a method for the production thereof. It consists of an inhalator housing, which has a housing part (1), in which there is formed at least one medicament chamber (11) with a dose of a powdered medicament, and wherein the inhalator housing has an outlet opening (13') and an outlet channel (13), which extends from the medicament chamber (11) to the outlet opening (13'). The outlet channel (13) is advantageously formed in the housing part (1). Also formed in the housing part (1) are an air inlet opening (12'), on a side of the medicament chamber (11) that is facing away from the outlet opening (13'), and an inlet channel (12), wherein the inlet channel (12) extends from the air inlet opening (12') to the medicament chamber (11).

15 Claims, 8 Drawing Sheets

(58) Field of Classification Search
CPC .......... A61M 15/0003; A61M 15/0008; A61M 15/002; A61M 15/0021; A61M 15/0028–0063; A61M 15/0086; A61M 15/0091; A61M 15/0096; A61M 15/08; A61M 2202/064; A61M 2202/14; A61M 2205/0205; A61M 2205/0216; A61M 2205/27; A61M 2205/273; A61M 2207/10; A61M 2210/06; A61M 2210/0618; A61M 2210/0625
See application file for complete search history.

(56) References Cited

U.S. PATENT DOCUMENTS

| | | | | |
|---|---|---|---|---|
| 5,533,505 | A * | 7/1996 | Kallstrand | A61M 15/0028 128/203.15 |
| 5,660,169 | A * | 8/1997 | Kallstrand | A61M 15/0028 128/203.15 |
| 5,918,594 | A * | 7/1999 | Asking | A61M 15/00 128/203.15 |
| 6,102,035 | A | 8/2000 | Asking et al. | |
| 6,105,574 | A * | 8/2000 | Jahnsson | A61M 15/0028 128/203.15 |
| 6,286,507 | B1 * | 9/2001 | Jahnsson | A61M 15/0028 128/203.15 |
| 6,397,838 | B1 * | 6/2002 | Zimlich, Jr. | A61M 15/0065 128/200.14 |
| 7,533,668 | B1 * | 5/2009 | Widerstrom | A61M 15/0028 128/203.12 |
| 8,985,118 | B2 * | 3/2015 | Nadershahi | A61F 6/202 128/869 |
| 9,447,987 | B1 * | 9/2016 | Arvey | F23L 13/00 |
| 2002/0092523 | A1 * | 7/2002 | Connelly | A61M 15/0028 128/203.15 |
| 2002/0108611 | A1 * | 8/2002 | Johnston | A61M 15/0028 128/203.15 |
| 2004/0158221 | A1 * | 8/2004 | Mizutani | A61F 13/47209 604/385.17 |
| 2005/0252510 | A1 * | 11/2005 | Young | A61M 15/0028 128/203.12 |
| 2006/0237010 | A1 * | 10/2006 | De Boer | A61M 15/0045 128/203.15 |
| 2007/0240713 | A1 * | 10/2007 | Boeck | A61M 15/0028 128/203.15 |
| 2008/0142009 | A1 | 6/2008 | Carrico et al. | |
| 2009/0056716 | A1 * | 3/2009 | Carrier | A61M 15/00 128/204.15 |
| 2009/0084379 | A1 * | 4/2009 | Goeckner | A61M 15/0028 128/203.15 |
| 2009/0235930 | A1 * | 9/2009 | Young | A61M 15/0028 128/203.15 |
| 2010/0059049 | A1 * | 3/2010 | Genosar | A61M 15/0065 128/203.15 |
| 2010/0124591 | A1 * | 5/2010 | Feldmeier | B65D 81/3244 426/120 |
| 2010/0139655 | A1 * | 6/2010 | Genosar | A61M 15/0065 128/203.15 |
| 2010/0313886 | A1 | 12/2010 | Wachtel et al. | |
| 2013/0291865 | A1 * | 11/2013 | Jones | A61M 15/00 128/203.15 |
| 2014/0083423 | A1 * | 3/2014 | Jung | A61M 15/0028 128/203.21 |

FOREIGN PATENT DOCUMENTS

| | | |
|---|---|---|
| RU | 2533727 | 11/2014 |
| WO | 2007/042822 | 4/2007 |
| WO | 2009/152477 | 12/2009 |
| WO | 2012/004485 | 1/2012 |
| WO | 2012/047182 | 4/2012 |
| WO | 2012/078804 | 6/2012 |
| WO | 2013/036881 | 3/2013 |

* cited by examiner

M1 — Shaping bottom film
M2 — Filling
M3 — Shaping and sealing aluminum foil and cover film
M4 — Sealing finished blister, punching, discharging

SINGLE-DOSE POWDER INHALATOR AND METHOD FOR THE PRODUCTION THEREOF

BACKGROUND OF THE INVENTION

The invention relates to a single-dose powder inhaler composed of an inhaler housing which has a housing part in which at least one medicament chamber having a dose of a pulverulent medicament is formed, and wherein the inhaler housing has an outlet opening and an outlet duct which extends from the medicament chamber to the outlet opening and further relates to a method for the production thereof.

The powder inhalers ("inhalers") that are commercially customary are frequently designed for multiple use and are therefore complicated and expensive to produce. Use as a disposable article is often not suitable. However, multiple use creates sometimes significant hygiene problems, since the patient cleans the inhaler incorrectly, rarely or not at all after use. A further problem is that caps can be lost. From a hygiene point of view, it is also unfavorable if the patient uses the inhaler wrongly, for instance breathes out into the inhaler: in known inhalers, patients do not always breathe out in the intended exhalation direction, but through the inhaler, such that the inhaler tends to clog up on account of the breath humidity upon multiple use, since the pulverulent medicament clumps and remains stuck in the air duct in the inhaler. These deposits and agglutinations, which can also be contaminated with pathological germs, can result in dosing inaccuracies and further drawbacks, for instance even for nasal application: there, nasal germs should be taken into consideration, for example when sinusitis proves to be resistant to treatment. It is possible for the person affected to repeatedly reinfect themselves (nasally, oropharyngeally) via the inhaler.

WO2007/042822 describes a single-dose powder inhaler which has a first housing part and a second housing part made of metal, which, joined together, form an inhaler housing with an outlet. The first housing part comprises a medicament chamber which contains a single dose of a pulverulent medicament and which is closed by a foil fastened to the first housing part. This foil extends out of the inhaler housing such that it can be gripped and pulled off for use by a user, with the result that the pulverulent medicament is released from the medicament chamber. The second housing part has a collection well and/or a dispersion chamber through which an air duct formed in the inhaler housing leads to the outlet. After the medicament chamber has been opened, an air flow is generated, upon inhalation at the outlet, through the gap between the housing parts which remains after the foil has been pulled off, said air flow entraining the pulverulent medicament released from the medicament chamber out of the collection well or the dispersion chamber.

Proceeding from this prior art, the object of the present invention is to a single-dose powder inhaler which is easy and cost-effective to produce, easy to use and is improved with regard to deagglomeration of the contained powder and completeness of powder emptying.

SUMMARY OF THE INVENTION

This object is achieved by a single-dose powder inhaler that is characterized in that the outlet duct is formed in the housing part and in that an air inlet opening on a side of the medicament chamber remote from the outlet opening, and an inlet duct which, extends from the air inlet opening to the medicament chamber, are formed in the housing part, wherein air-guiding, turbulence-inducing and/or deflecting structures are formed in the air inlet duct, in the medicament chamber, and in the outlet duct, and the inlet duct narrows from the air inlet opening to the medicament chamber and the outlet duct widens from the medicament chamber in the direction of the outlet opening.

The object of producing such an inhaler is achieved by the method comprising the steps of producing the housing part from plastic by injection-molding or preferably by thermoforming a plastic film, filling the medicament chamber with a dose of a pulverulent medicament, closing the medicament chamber with a film element, by two plug elements and/or by a fold, received in a blocking duct, of the covering element, and cutting out the extensive and substantially planar covering element or producing the shaped cover element from plastic by injection-molding or preferably by thermoforming a plastic film, attaching the covering element to the housing part.

wherein the method is carried out in a single device.

Developments of the device are specified in the dependent claims.

A single-dose powder inhaler according to the invention consists of an inhaler housing which has a housing part in which at least one medicament chamber is formed which contains a full dose or partial dose of a pulverulent medicament. The single-dose powder inhaler according to the invention is thus, as it were, an inhaler that is usable in a blister-free manner, that is to say without the use of a separate blister filled with medicament. The inhaler housing has an outlet opening and an outlet duct which extends from the medicament chamber to the outlet opening. According to the invention, not only is the outlet duct also formed in the housing part, but also an air inlet opening on a side of the medicament chamber remote from the outlet opening and an inlet duct which extends from the air inlet opening to the medicament chamber. It is thus possible for all the portions that are relevant for the powder inhaler to be formed in a single housing part, which is then merely covered with a covering element after the medicament chamber is filled with a dose of powder. In order to support and improve the deagglomeration, uniform dispersion and complete emptying of the powder when the single-dose powder inhaler is used, air-guiding, turbulence-inducing and/or deflecting structures are formed in the housing part in the air inlet duct, in the medicament chamber and in the outlet duct, in order to influence the air flow into, through and out of the medicament chamber. In order to control the flow rate, provision is also made for the inlet duct to narrow from the air inlet opening to the medicament chamber and for the outlet duct to widen from the medicament chamber in the direction of the outlet opening. As a result, all the structures that are required for an optimally functioning powder inhaler are advantageously provided in one housing part, such that, in order to complete the powder inhaler, all that is necessary is also a single further component, i.e. the covering element. In other words, the powder inhaler according to the invention advantageously simply consists of just two housing parts, which can additionally be produced and joined together in a simple manner. The powder inhaler can therefore be manufactured in an extremely cost-effective manner and is therefore suitable for administering a dose of powder (or a combination of several doses of powder) in a single use with the associated hygienic advantages for the user. A powder inhaler according to the invention therefore not only provides the structures that are required for optimal administration of a pulverulent medicament by inhalation but also represents a blister pack for the pulverulent medicament.

Preferably, the housing part can cost-effectively consist of plastic and be manufactured in an injection-molding process or preferably by shaping, particularly preferably by thermoforming, a pharmaceutically compliant, preferably single-type plastic film. To cover the housing part in order to bound the air inlet duct, the medicament chamber and the outlet duct and to complete the housing part to form the inhaler housing, a covering element is provided which can be formed easily and cost-effectively in an extensive and substantially planar and unshaped manner. "Substantially planar and unshaped" is intended here to mean that the covering element can be completely flat in the simplest and preferred variant; however, provision can also be made for the covering element to have for example a longitudinal curvature along the air inlet duct, the medicament chamber and the outlet duct both for stabilization and for flow optimization. Alternatively, however, the covering element can also be formed in a manner corresponding to the housing part, at least in the region of the inlet duct and of the outlet duct. Like the latter, the covering element can therefore likewise consist of plastic and be manufactured in an injection-molding process or preferably by shaping, particularly preferably by thermoforming, a pharmaceutically compliant, preferably single-type plastic film. The structure of a powder inhaler according to the invention thus corresponds to that of a buster pack. In this case, at least one of the two inhaler housing components, namely the housing part and covering element, can be embodied in a transparent manner, such that the powder present in the medicament chamber and the administration thereof can be checked by sight. Preferably, therefore, at least the housing part can be shaped from a transparent plastic film which is covered with an aluminum foil or plastic film, such that only the air inlet opening and outlet opening remain open. If a plastic film is used for covering, this can preferably consist of the same plastic as the first housing part, such that the powder inhaler can be readily recycled after use. Of course, a composite film can also be used as the covering element; however, this is not preferred on account of its poorer recyclability. The material selection for the covering element depends on whether it is intended to be a shaped or a substantially planar covering element. If the covering element is shaped, the preferred material is a plastic thermoforming film corresponding to the housing part, such that the shaped covering element is dimensionally stable.

The covering element can additionally be advantageously printed in order to provide the user with information about the content and use of the inhaler. This information can be provided by text or preferably supported by graphics and optionally colors in order to be internationally understandable. If appropriate, information can also be provided in the film in Braille.

Provision can also be made for the housing part to be produced from an opaque or colored plastic. In this way, differently colored plastics can also provide information about the type and/or quantity of contained powder medicament.

The outlet opening can be formed as a mouthpipe or be connected to a nose nozzle. In addition to the inlet duct narrowing from the air inlet opening to the medicament chamber and the outlet duct widening from the medicament chamber in the direction of the outlet opening (said outlet duct optionally narrowing again if a nose nozzle is present), a cross section of the air inlet duct at the medicament chamber can also preferably be kept smaller than a cross section of the outlet duct at the medicament chamber in order to control the flow rate.

In order to support the deagglomeration of the powder in the medicament chamber when the single-dose powder inhaler is used, at least one loose deagglomerator can be arranged therein, which is swirled up with the powder by the turbulent air flow which is generated by the shape of the air inlet duct in the medicament chamber, and breaks up powder agglomerates. Preferably, a deagglomerator has large enough dimensions for it to remain in the medicament chamber and not to be able to pass into the air inlet duct or into the outlet duct. Optionally, the deagglomerator can be embodied with apertures, i.e. in an air-permeable manner, such that an air flow is not blocked, even when the deagglomerator comes to rest in front of the outlet opening of the medicament chamber.

According to the invention, provision is made for the medicament chamber of the single-dose powder inhaler to be closed after being filled with the dose of powder (and optionally also with the deagglomerator), such that the filled single-dose powder inhalator can be stored until it is used. This closure is intended to be opened when the powder inhaler is intended to be used for the inhalation of the contained powder. For the purpose of the closure, different variants are provided according to the invention.

A variant that is preferred on account of easy operability for the user comprises a film element (peeling film), for example made of aluminum or plastic, with a closure tab that closes the medicament chamber.

Such a film element can have a pull-off tab connected to the closure tab via a tape portion, said pull-off tab extending out of the air inlet opening or outlet opening from one side of the medicament chamber through the opposite air inlet duct or outlet duct. In other words, either the tape portion extends out of the air inlet opening from the outlet side of the medicament chamber through the air inlet duct with the pull-off tab, or preferably out of the outlet opening from the inlet side of the medicament chamber through the outlet duct, since the duct cross section is larger on the outlet side of the medicament chamber. If traction is exerted on the pull-off tab, the closure element is pulled off the medicament chamber, such that the powder medicament is released, and can be removed from the inhaler housing.

As an alternative to the pull-off tab, in order to open the closure tab which closes the medicament chamber, provision can be made for the covering element to be formed, on the opposite side from the medicament chamber, into a resilient pressure element which has, on its inner side, as side facing the medicament chamber, one or more piercing elements in order for it to be possible to preferably perforate the closure tab by pressure being exerted on the pressure element.

As an alternative to a film element, the medicament chamber can be closed by two plug elements, wherein each plug element has a plug portion which is arranged in a portion, adjacent to the medicament chamber, of the air inlet duct and of the outlet duct: furthermore, the plug element has a pull-off tab which extends in each case out of the air inlet opening and the outlet opening. In order to make the powder inhaler ready for inhalation, in this case the plug portions are removed from the air inlet duct and the outlet duct by traction on the pull-off tabs.

In a further, but technically more complicated alternative for closing the medicament chamber, a laterally bounded blocking duct is formed in the housing part on both sides of the medicament chamber transversely or at right angles to the air inlet duct and the outlet duct, said blocking duct conferring increased stability on the housing part as a result and a correspondingly formed fold of the covering element being received in said blocking duct in a manner closing the air inlet duct and the outlet duct in a sealing manner. In order that these folds can be lifted out of the blocking duct in order to free up the air inlet duct and the outlet duct to open the medicament chamber, the powder inhaler has a lifting element for which again different embodiments are provided according to the invention.

A lifting element of a powder inhaler according to the invention can be at least one predetermined and marked pressure, bending or pulling point on the inhaler housing, i.e. on the covering element, such that the folds are lifted out of the blocking ducts by exertion of pressure or traction or bending at particular points of the inhaler housing.

As an alternative thereto, a pull tape can be provided as lifting element, said pull tape extending through the air inlet duct and the outlet duct and transversely through the blocking duct between the fold of the covering element and the housing part. This pull tape can have a grip portion at both ends such that both ends of the pull tape are pulled simultaneously in order to lift the folds. As an alternative, which is preferred on account of easier handling, the pull tape can have a grip portion only at one end, while the other end is anchored to an anchoring structure of the inhaler housing. This anchoring structure can be configured at the same time as an air deflection or guiding structure in the air inlet duct or outlet duct.

Furthermore, it is also possible for the above-described plug elements to be used as lifting elements in that they lift the fold while being pulled out of the duct portions adjacent to the medicament chamber.

Finally, it is also conceivable for a structure arranged loosely in the medicament chamber, it preferably being possible for said structure to be the deagglomerator, to be used to lift the fold.

Although a powder inhaler according to the invention is designed to be used once, in the preferred cost-effective embodiment with the single-type plastic thermoforming film for the housing part and aluminum foil or plastic film for the covering, the components are highly suitable for recycling. In addition, provision can also be made for the plastic used for production to preferably be able to be biodegradable if it is not supplied for recycling.

In order to meet higher hygienic requirements, the plastic used can be an antiseptic and/or antimicrobial plastic. As an alternative thereto, at least the air inlet duct, the medicament chamber and the outlet duct, and also the mouthpiece or nosepiece, can be provided with an antiseptic and/or antimicrobial coating.

For protection against counterfeits, the plastic can also contain a marker which can be verified on the finished powder inhaler.

Finally, for instance when two or more active ingredients are intended to be administered at the same time, the medicament chamber can be subdivided into at least two subchambers by at least one partition wall or two or more medicament chambers can be formed in the housing part, which are arranged in parallel alongside one another in each case with an air inlet duct and an outlet duct or be arranged in series with one another, wherein the air inlet duct leads to the first medicament chamber and the outlet duct extends from the last medicament chamber and the medicament chambers are connected together via a further duct. However, it is also possible for a division of a larger single dose between several medicament chambers to be more advantageous in terms of flow, in order to achieve complete deagglomeration and emptying and also uniform dispersion and thus inhalation of the contained powder.

A single-dose powder inhaler according to the invention can thus contain a full dose of a pulverulent medicament in a single medicament chamber or contain a partial dose in each case in two or more subchambers or parallel or serial medicament chambers, said partial doses being inhaled simultaneously upon use.

If the subchambers are closed by a film element or the several chambers are closed by several film elements, the shaped covering element can be equipped with piercing elements in a corresponding, manner in order to open the film elements. In other words, if a medicament chamber is subdivided into subchambers by one or more partition walls, at least one piercing element is provided for each subchamber on the pressure element, which is formed opposite the medicament chamber in the covering element, such that upon pressure on the pressure element, the film element over each subchamber is perforated and thus the pulverulent substance present therein can be released. If a housing part with several powder chambers is provided, a corresponding number of pressure elements with the respective at least one piercing element are provided on the shaped covering element.

A method according to the invention for producing a single-dose powder inhaler according to the invention can advantageously be carried out in a single device. This is accordingly a blister machine for film thermoforming, filling and sealing. The method first of all provides the injection-molding or—preferably—thermoforming of the housing part from plastic, whereupon the medicament chamber is filled with a dose of a pulverulent medicament. In parallel with the manufacture of the housing part and/or filling, the covering element is manufactured, depending on the embodiment, from a film simply by a separating method such as cutting or punching of the extensive and substantially planar covering element or from plastic by injection-molding or—preferably—thermoforming. After the medicament chamber has been closed with a film element, wherein the closure tab is sealed or adhesively bonded to the medicament chamber, the covering element is attached to the housing part, preferably likewise by sealing, adhesive bonding or by welding (e.g. ultrasonic welding). When the medicament chamber is closed with a film element, which is provided so that the medicament chamber is opened by pulling off the closure tab, before the covering element is attached, the tape portion leading to the pull-off tab is folded or turned down, such that the pull-off tab projects out of one of the openings in the housing part. As an alternative to the film element, the medicament chamber can optionally also be closed by two plug elements and/or by a fold, received in a blocking duct, of the covering element.

This simple method allows extremely cost-effective production of the powder inhaler and is further quick and easy to adapt to different variants such that patient-specific embodiments and fillings are also economically possible. Furthermore, this powder inhaler, which combines cost-effective production with optimal release of powder, is thus also suitable for sale or distribution in Third World countries.

Further embodiments and some of the advantages which are associated with these and further embodiments are understandable clearly and better from the following detailed description with reference to the accompanying figures. Objects or parts thereof which are substantially identical or similar can be provided with the same reference

DESCRIPTION OF PREFERRED EMBODIMENTS

The device according to the invention concerns a powder inhaler that is simple and cost-effective to produce and consists of two housing parts, a shaped housing part and a covering element, which, joined together, form the inhaler housing. The powder inhaler according to the invention can be embodied in the manner of a blister pack, wherein the housing part or the covering element or both are transparent and thus make(s) it possible to see into the powder inhaler, in particular into the medicament chamber. With the inhaler configured in an at least partially transparent manner, it is possible to check the content or the complete emptying of the content in use. In addition, the turbulence during use can be monitored.

The housing part is formed to provide the air inlet duct, the medicament chamber and the outlet duct and can advantageously be manufactured cost-effectively by a plastic thermoforming film or optionally also be produced in a plastic injection-molding process.

In order to bound the air inlet duct, the medicament chamber and the outlet duct, a pharmaceutically compliant film, which can be an aluminum foil, composite film or (transparent) plastic film, can simply be attached, for example by sealing, welding or adhesive bonding, as covering element to the housing part.

Figure 1:
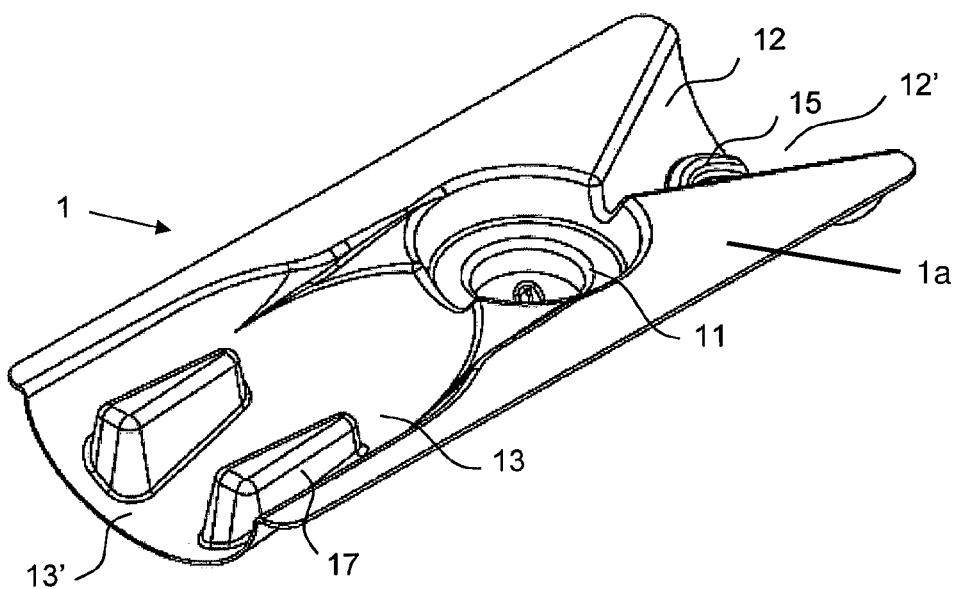
FIG. 1 shows a perspective view of the housing part of a single-dose powder inhaler according to the invention.
Figure 2:
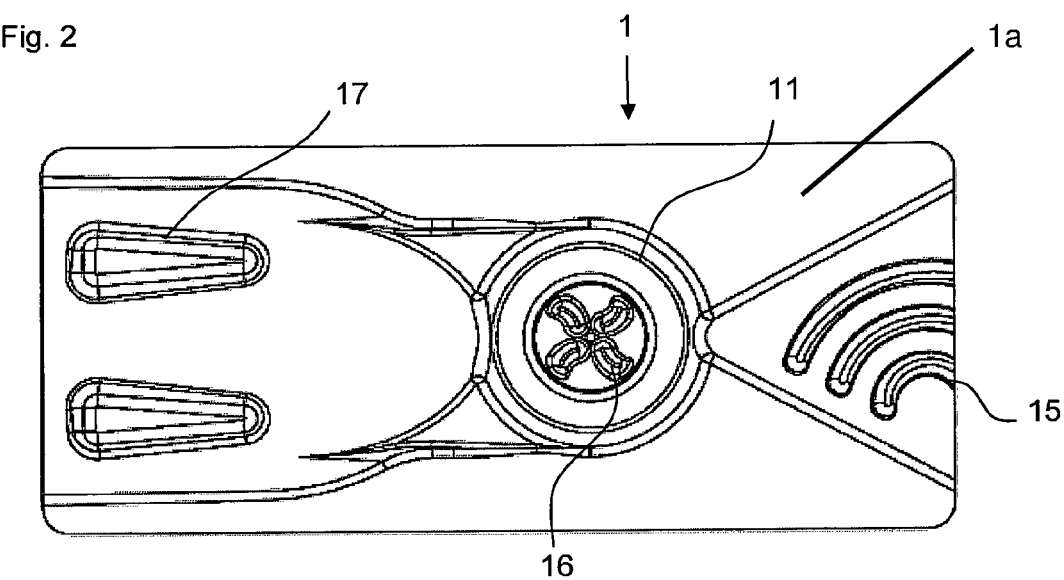
FIG. 2 shows a plan view of the housing part from FIG. 1.
Figure 3:
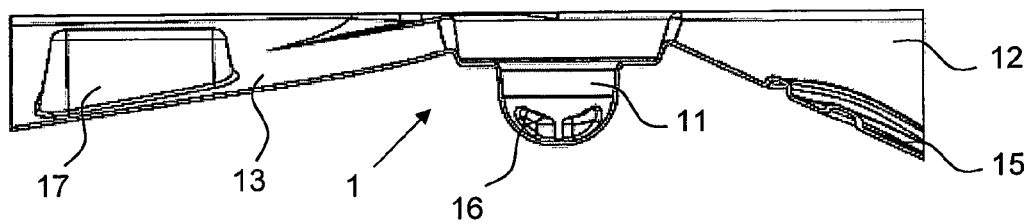
FIG. 3 shows a view in longitudinal section through the housing part from FIG. 1.

FIGS. 1 to 3 show an example of a housing part 1 as is used to produce a powder inhaler according to the invention. The housing part 1, shaped here from thermoforming film, has a half-funnel-shaped air inlet duct 12, which extends from an air inlet opening 12' to the medicament chamber 11, which is formed exclusively in the housing part 1 in a cup-shaped manner. On the side away from the air inlet, the outlet duct 13 extends from the medicament chamber 11 to the outlet opening 13', which in this case has a semioval cross section in order to be able to be received readily in the mouth.

Formed in the air inlet duct 12 are a plurality of air guiding structures 15 in order to swirl up the air flow drawn in during use before it reaches the medicament chamber 11. Formed in the base of the medicament chamber 11 are turbulence-inducing structures 16 which improve the deagglomeration of the swirled-up powder. A widening of the outlet duct 13 next to the medicament chamber 11 ensures a spacer effect, wherein not only is the flow rate that is increased beforehand by the funnel-shaped inlet slowed down, but also the entrained powder is distributed uniformly. This effect is supported by the guiding structures 17 which additionally give the housing part 1 increased stability in the outlet region.

Following the production of the housing part 1, which preferably takes place by thermoforming film, but can optionally also take place by injection-molding, the medicament chamber 11 is filled (not illustrated in the figures) with a dose of powder (and optionally also with a loose deagglomerator) and subsequently closed.

The medicament chamber 11 can be closed in different ways.

Figure 4:
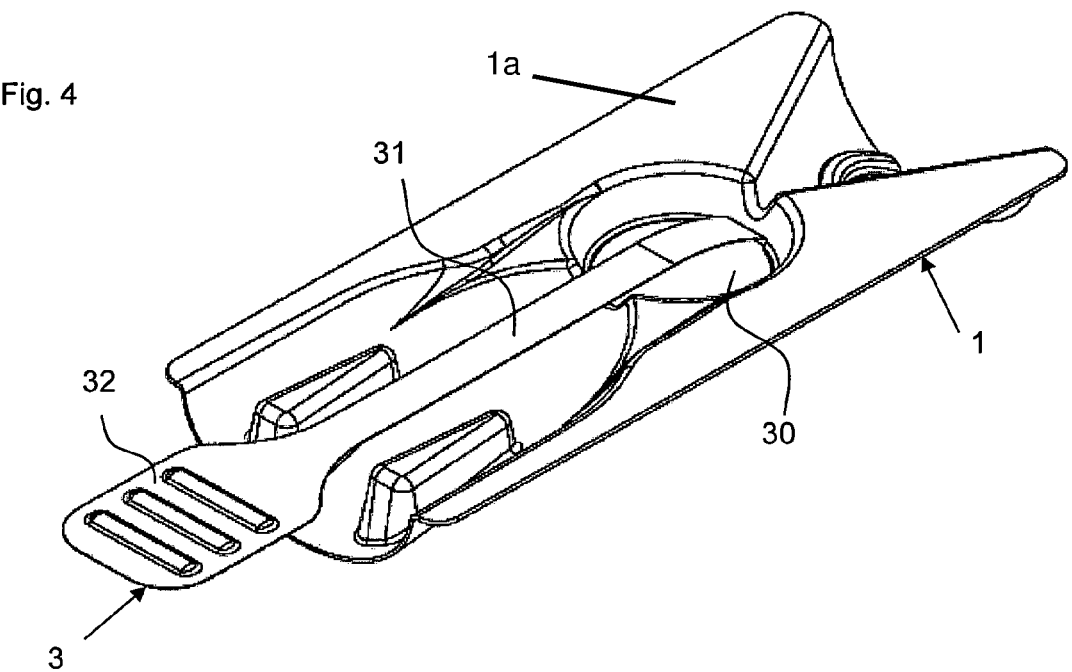
FIG. 4 shows a perspective view of the housing part from FIG. 1, in which the medicament chamber has been closed with a film element.
Figure 5:
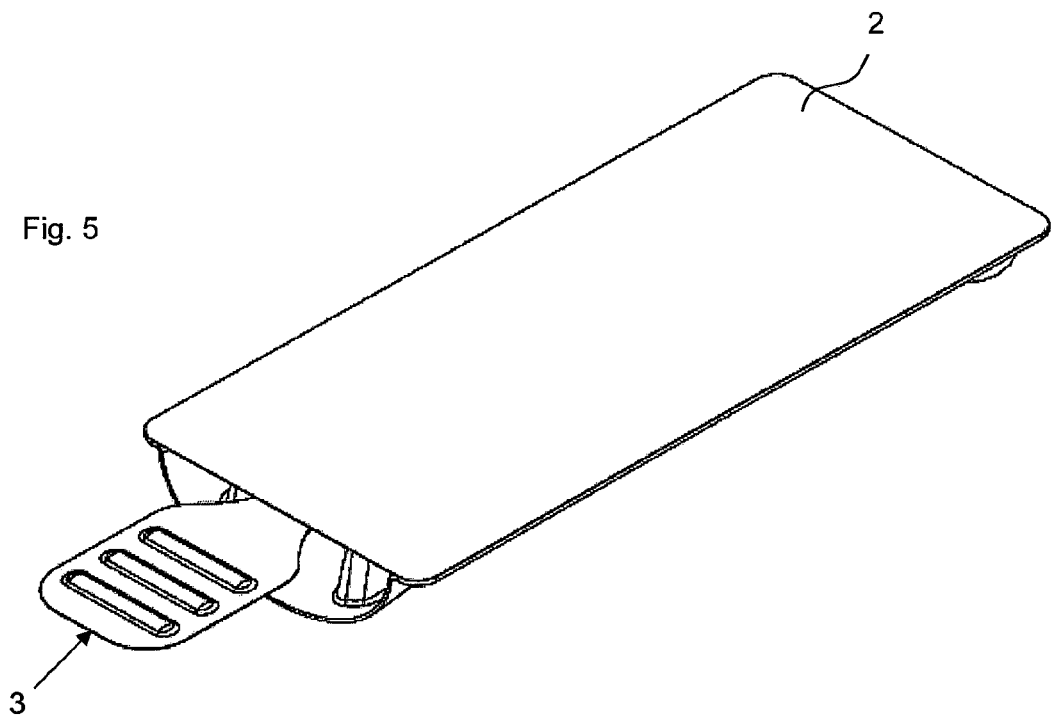
FIG. 5 shows a perspective view of a powder inhaler according to the invention, having the housing part from FIG. 4, which has been dosed with a planar (aluminum) foil as covering element.
Figure 6:
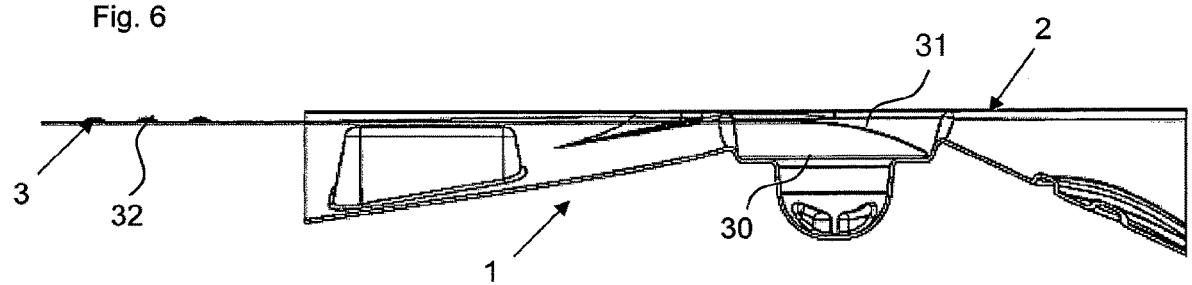
FIG. 6 shows a view in longitudinal section through the powder inhaler according to the invention from FIG. 5.

FIGS. 4 to 6 show an embodiment in which, in order to close the medicament chamber 11, which is exclusively formed in the housing part 1, a film element 3 is used. The film element 3 has a closure tab 30, which is dimensioned such that it closes the medicament chamber 11. From this closure tab 30, a tape portion 31 extends to a pull-off tab 32, which is ribbed here for a secure grip. In this case, the tape portion 31 is folded over on the closure tab 30 such that the pull-off tab 32 projects out of the housing part 1 on the side away from the folded-over end. In the example shown, the tape portion 31 is deflected on the inlet side of the closure tab 30 and projects, with the pull-off tab 32, out of the outlet opening 13'.

In general, it is also conceivable for such a film element 3 to also be able to be arranged the other way round, such that the pull-off tab 32 projects out of the inlet opening 12'; however, since the cross section of the outlet duct 13 at the medicament chamber 11 is preferably larger than the cross section of the inlet duct 12, the outlet duct 13 lends itself to pulling off the closure tab 30. The closure tab 30 can be sealed, welded or adhesively bonded to a wall portion or an encircling shoulder of the medicament chamber 11, wherein the connection is embodied in a leaktight but also releasable manner, such that the closure tab 30 can be detached by traction on the pull-off tab 32, without tearing.

The example illustrated in FIGS. 1 to 6 represents a preferred variant of a powder inhaler according to the invention, which, on account of the blister-type structure, can be produced extremely simply and cost-effectively in a single machine and can additionally be operated easily and intuitively by the user.

Figure 7:
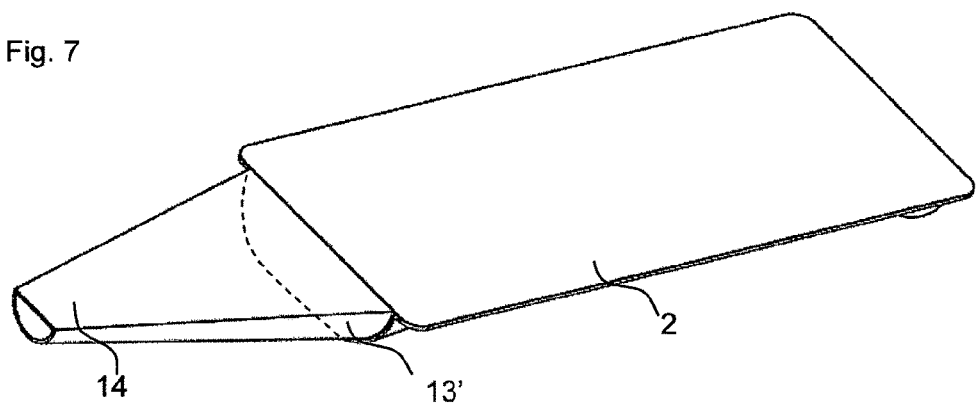
FIG. 7 shows a perspective view of a powder inhaler according to the invention with an outlet formed for nasal use.

FIG. 7 illustrates, by way of example, that a powder inhaler according to the invention can be formed not only with an outlet which is shaped to be received in the mouth. The (notional) outlet opening 13' (illustrated by a dotted line) can be adjoined by an outlet piece 14 formed for nasal use, which can extend away integrally from the housing part or can be placed on the outlet opening 13'.

Figure 8:
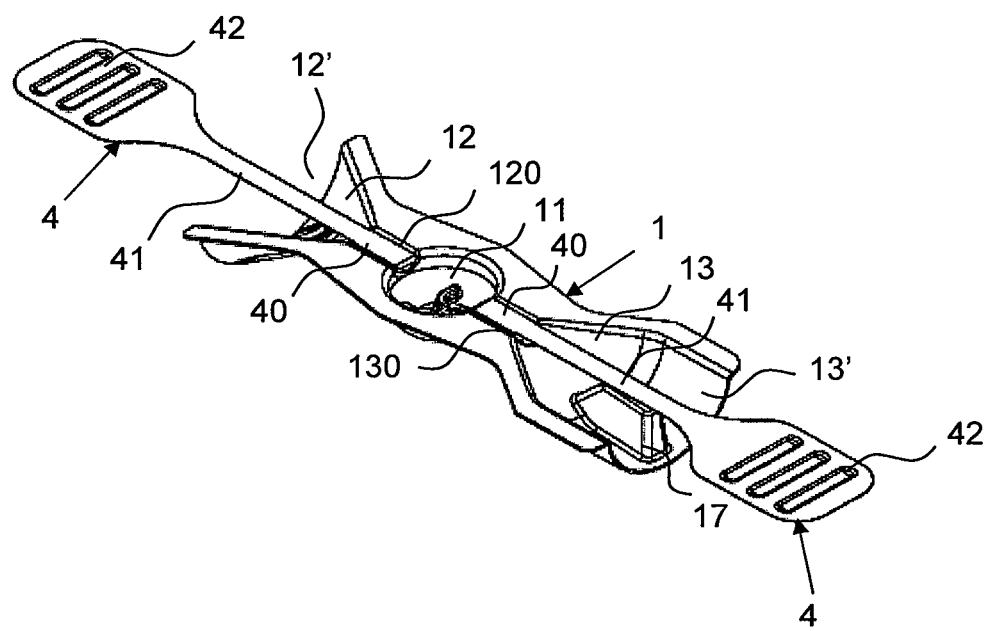
FIG. 8 shows a perspective view of a housing part in which two plug elements have been provided to close the medicament chamber.
Figure 9:
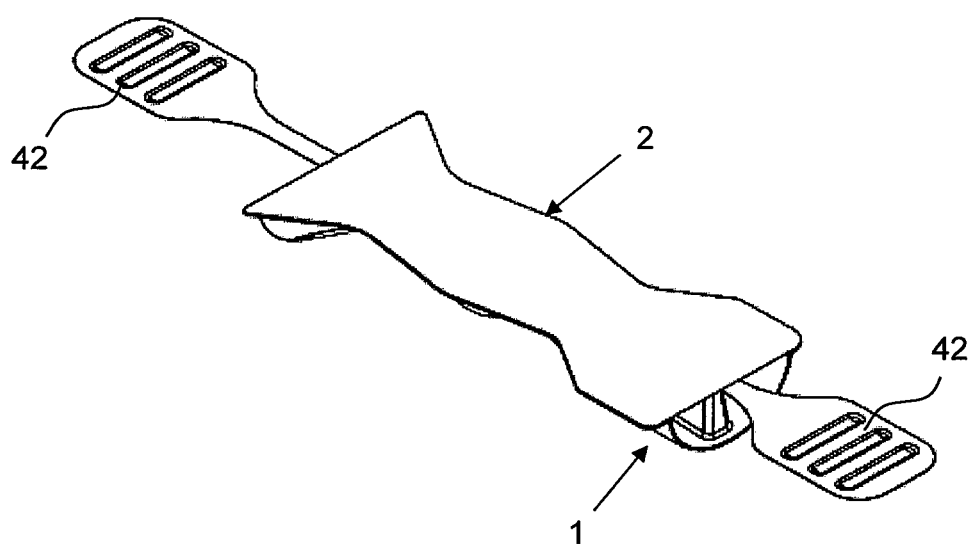
FIG. 9 shows a perspective view of a powder inhaler according to the invention, having the housing part from FIG. 8, which has been dosed with a planar (aluminum) foil as covering element.

FIGS. 8 and 9 show a variant of a powder inhaler according to the invention, in which the medicament chamber 11 is closed by two plug elements 4 before the covering element 2 covers the air inlet duct 12, the medicament chamber 11 and the outlet duct 13. The plug elements 4 each have a plug portion 40, from which a tape portion 41 extends to a pull-off tab 42. The plug portion 40 of each plug element 4 is arranged in a portion 120, 130, adjoining the medicament chamber 11, of the air inlet duct 12 and of the outlet duct 13 and is dimensioned and shaped such that it closes this portion 120, 130. A material of the plug portions 40 is chosen so as to allow a leaktight closure, although this can be overcome by traction on the pull-off tabs 42. Alternatively, an adhesive or sealing means can be introduced between the plug portion 40 and duct portion 120, 130, said adhesive or sealing means allowing the nondestructive removal of the plug portions 40 upon traction on the pull-off tabs 42.

Figure 10:
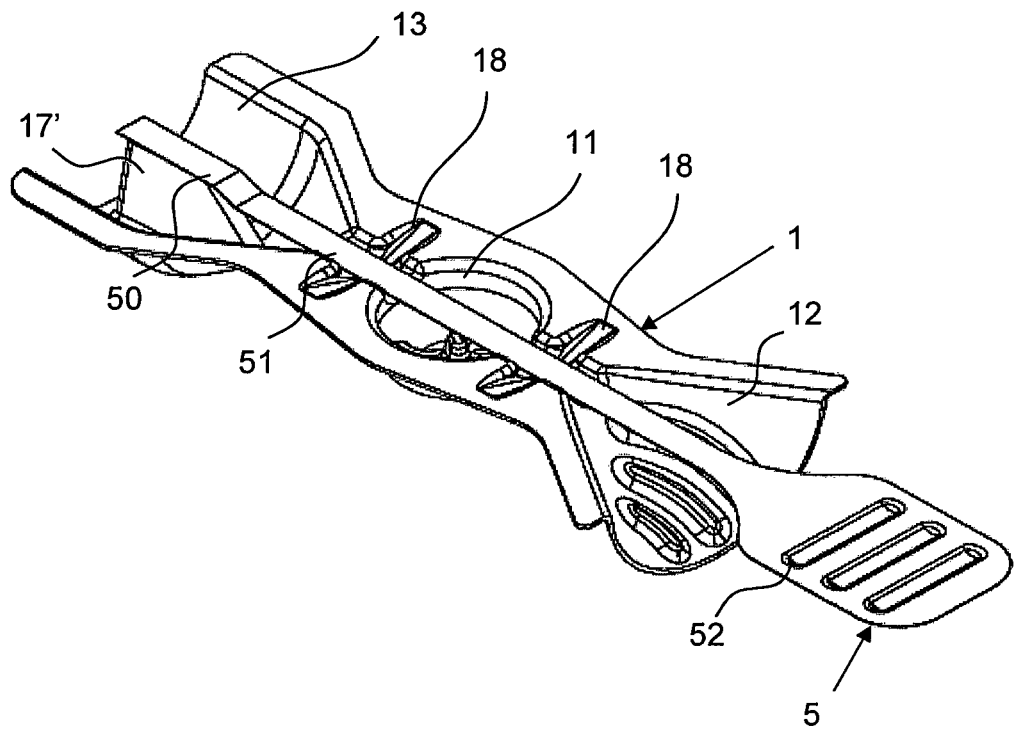
FIG. 10 shows a perspective view of a housing part, in which two blocking ducts are provided to close the medicament chamber and a pull tape is provided to open it.
Figure 11:
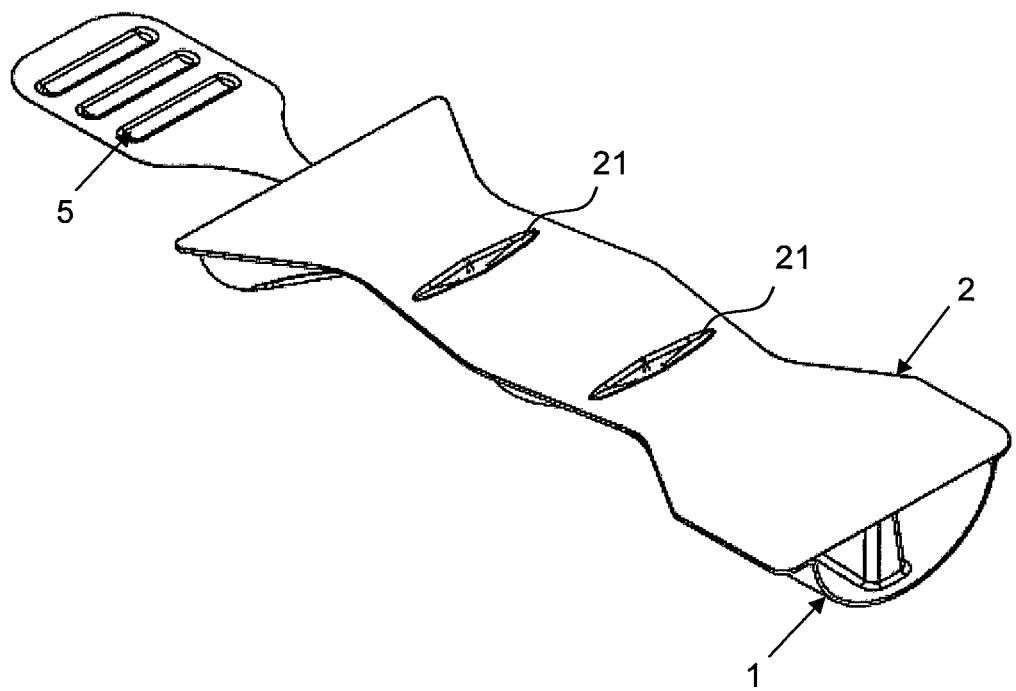
FIG. 11 shows a perspective view of a powder inhaler according to the invention, having the housing part from FIG. 10, which has been closed with a planar (aluminum) foil as covering element, the folds of which are received in the blocking ducts.

A further alternative for the closure of the medicament chamber is shown in FIGS. 10 to 13. FIGS. 10 and 11 reveal a housing part 1, in which, in the portions 120, 130 of the air inlet duct 12 and of the outlet duct 13 that are adjacent to the medicament chamber 11, a blocking duct 18 extending transversely thereto is formed. The substantially planar covering element 2 has, at points corresponding to these blocking ducts 18, integrally formed folds 21 which fill the blocking ducts 18 and thus block the portions 120, 130 of the air inlet duct 12 and of the outlet duct 13, thereby closing the medicament chamber 11. In order to open, a medicament chamber 11 closed in such a way and to clear the air inlet duct 12 and the outlet duct 13, the folds 21 are lifted out of the blocking ducts 18, to which end different variants according to the invention are provided.

To this end, in the example shown in FIGS. 10 and 11, a pull tape 5 is provided, the tape portion 51 of which extends from the outlet duct 13, transversely through the blocking ducts 18 and the medicament chamber 11, to the air inlet duct 12. The pull tape 5 is fastened by an end portion 50 to an anchoring structure 17' in the outlet duct 13, said anchoring structure 17' simultaneously serving as an air guiding structure. At the other end of the pull tape 5, a tab 52 projects out of the air inlet duct 12. The tape portion 51 is pushed into the blocking ducts 18 with the folds 21 when the covering element 2 is arranged. In order to clear the air inlet duct 12 and the outlet duct 13, traction is exerted on the tape portion 51, held on the anchoring structure 17', at the tab 52, such that the tape portion 51 can lift the folds 21 out of the blocking ducts 18. Other than as illustrated, such a pull tape can also be embodied in an unanchored manner with two tabs, such that, in order to lift the folds 21 and clear the air inlet duct 12 and the outlet duct 13, the two tabs are pulled.

Figure 12:
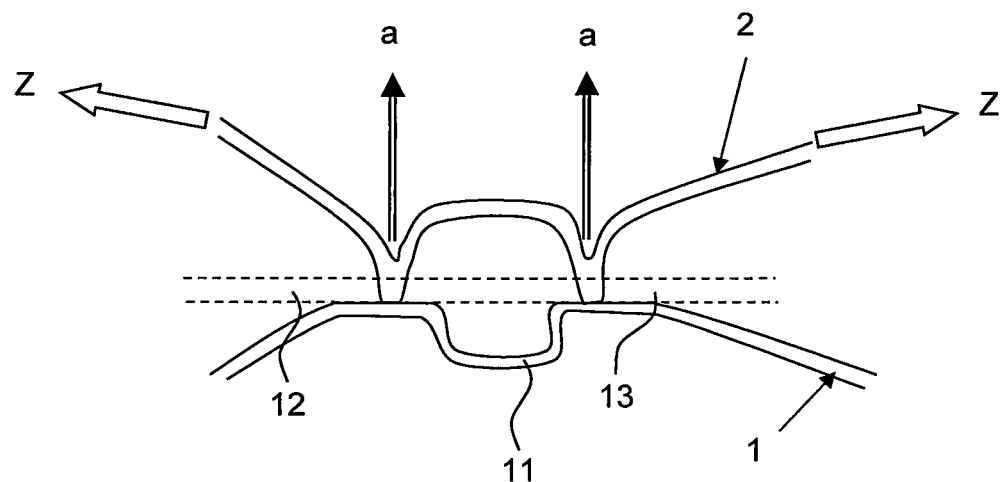
FIG. 12 shows a schematic sectional side view of a powder inhaler according to the invention, in which the medicament chamber has been closed by folds in the covering element in the blocking ducts, which are lifted by traction on the covering element.
Figure 13:
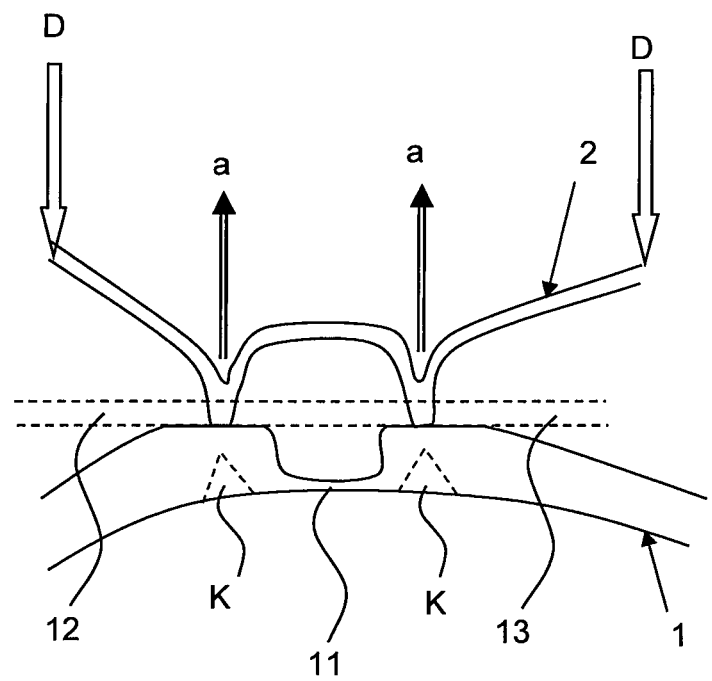
FIG. 13 shows a schematic sectional side view of a powder inhaler according to the invention, in which the medicament chamber has been closed by folds in the covering element in the blocking ducts, which are lifted by pressure on the covering element and bending elements.

As an alternative thereto, it is possible, as indicated in FIG. 12, to exert the traction force Z on the covering element 2 in order to lift the folds, as indicated by the double arrow a. However, provision can also be made for pressure D to be exerted on the covering element 2 at particular points in order to lift the folds and/or to bend the housing at the points K provided for this purpose.

A further possibility for clearing the flow duct through the air inlet duct 12 and outlet duct 13 and opening the medicament chamber 11 consists in detaching plug elements (as described above) in order to lift the folds. Furthermore, a preferably spherical structure which is arranged loosely in the medicament chamber and is thus freely movable and which also acts as a deagglomerator in use, can be used, by lifting, to lift the folds in the blocking ducts.

In general, a powder inhaler according to the invention can differ from the exemplary embodiments shown, and thus the invention is not limited to the numbers and shapes, shown in the figures, of the air-turbulence-inducing, deflecting and guiding structures 15, 16, 17 and 17'; the structures of the inner wall of a single-dose powder inhaler according to the invention that are formed in the air inlet duct 12, in the medicament chamber 11 and the outlet 13 in order to improve the aerodynamics, resistance and/or deagglomeration can differ as intraluminal flow elements from the shapes illustrated and be formed for example as chicanes, blades, helices, spirals or meanders.

Furthermore, the flow profile through the medicament chamber can be aerodynamically adjusted to resistance, throughflow and powder by variations in the bore profile with regard to size, shape and edge design (sharp-edged, beveled or rounded) at the inlet and outlet of the medicament chamber. Thus, different factors influence the air flow in terms of speed and course through the powder inhaler and in particular the medicament chamber, these factors influencing the completeness of emptying and deagglomeration and dispersion in the air flow, for example the narrowing cross-sectional profile in the air inlet and the widening cross section in the outlet, wherein the flow duct is preferably narrower on the inlet side of the medicament chamber than on the outlet side.

Figure 14:
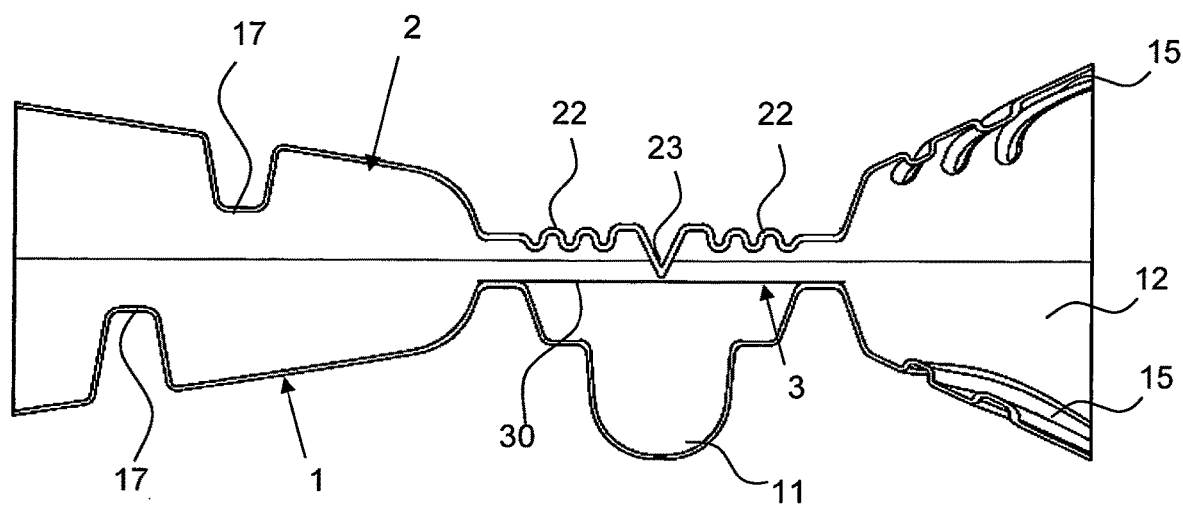
FIG. 14 shows a view in longitudinal section through a powder inhaler according to the invention, having a shaped cover element which has a pressure element with a piercing element for opening the closure tab.
Figure 15:
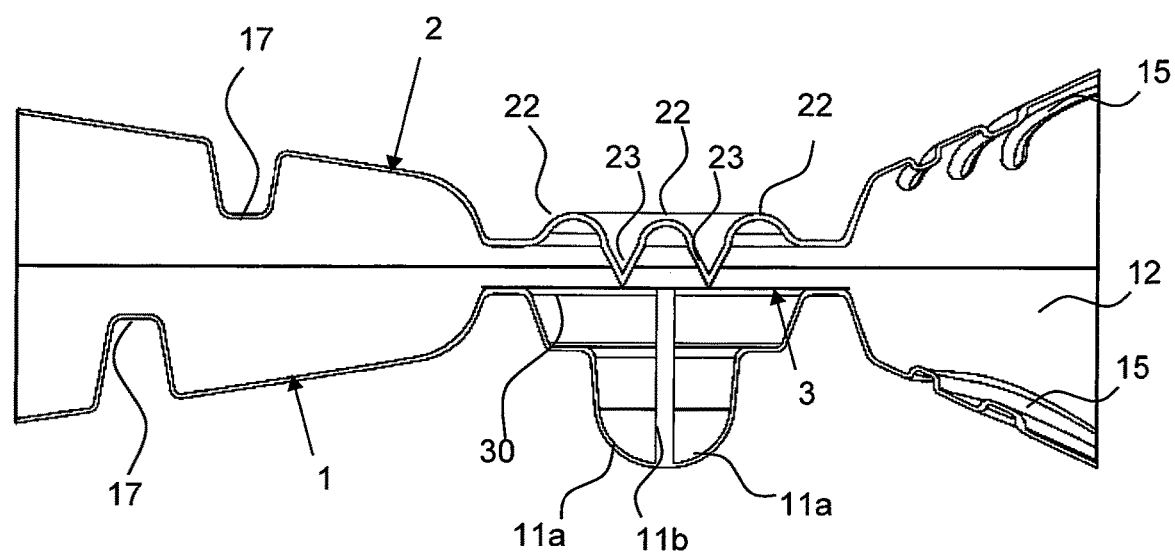
FIG. 15 shows a view in longitudinal section through a further powder inhaler according to the invention, having a shaped cover element, in which the pressure element has two piercing elements for opening the closure tab over the two subchambers.

FIG. 14 and FIG. 15 show powder inhalers according to the invention, in which not only the housing part 1 with the medicament chamber 11 but also the covering element 2 is shaped. In this embodiment, the respective portions on the housing part 1 and covering element 2 for forming the air inlet duct 12 and the outlet duct 13 correspond to one another both in terms of opening angle and in the formed air-turbulence-inducing, deflecting and guiding structures 15, 17. The covering element 2 differs from the housing part 1 only in the portion located between the inlet duct 12 and the outlet duct 13: instead of the medicament chamber 11, the covering element 2 has a region formed as a resilient pressure element 22, which has a central piercing element 23 directed inward in the direction of the medicament chamber 11 in FIG. 14 and two piercing elements 23 in FIG. 15, said piercing elements 23 being located respectively opposite the two subchambers 11*a* which are formed in the medicament chamber 11 by the partition wall 11*b*.

The pressure element 22 is formed by concentric circular wall structures which allow elastic deformation of the plastic film at this point, such that the inwardly integrally formed piercing element 23 can be moved in the direction of the medicament chamber 11 by exertion of pressure in order to pierce the closure tab 30 and returns to its starting position once the pressure has been released. The piercing element can consist of one or more needles or be formed by an angular structure such as a pyramidal spike. If, for the purpose of opening, pressure is exerted on both sides, i.e. pressure on the pressure element 22 and counterpressure on the medicament chamber 11, the closure tab 30, which can consist for example of aluminum foil, is effectively forced open, since the closure tab 30 is placed under tension by the counterpressure on the medicament chamber 11 and cannot yield to the piercing element 23.

The housing part and the covering part of a single-dose powder inhaler according to the invention can be welded together by heat, but adhesive bonding, clamping connections (wherein the periphery of one housing part is bent around the periphery of the other housing part), latching connections or stitched connections also come into question.

The powder inhaler according to the invention is provided for single use, and so the inhaler housing cannot be used again after the medicament chamber has been opened and the dose of powder has been inhaled, this also serving to protect against misuse. In addition to good recyclability or biodegradability, the increased volume of packaging waste, which is considered a drawback from the point of view of environmental protection, is also put into perspective, however, by the reduced use of multidose inhalers, the disposal of which is more complicated since residual quantities of the pulverulent medicament are usually contained therein.

The single-use powder inhaler according to the invention allows economical use for various indications—for instance when only a few uses are necessary, or only as required, for example in the case of migraine, pain, immunomodulators, biopharmaceuticals or the administration of CNS substances. The powder inhaler according to the invention is hygienic and undesired influences such as high air humidity or soiling on account of misuse are largely precluded.

On account of the cost-effective production, the powder inhaler according to the invention is also suitable for use in the Third World and in crisis areas.

In fact, the powder inhaler according to the invention is so reasonable to produce that patient-specific medication packs can be realized in an economically justifiable manner. The composition and dosing of the pulverulent medicament (or plurality of medicaments) can thus be filled into the powder inhaler according to the invention in a specific manner tailored to each patient.

In connection with FIGS. 1 to 14, exemplary embodiments of a single-dose powder inhaler according to the invention having, a single medicament chamber in which a dose of powder is present are shown. FIG. 15 shows a variant of the invention in which the medicament chamber 11 is subdivided into two subchambers 11*a* by the partition wall 11*b* formed in this case integrally with the housing part 1, such that two different pulverulent substances or medicaments, which need to be stored separately from one another, can come together upon inhalation only after the closure tab has been opened.

However, it is also conceivable according to the invention for two or more medicament chambers to be formed in the housing part which are arranged in parallel or in series in the flow duct between the air inlet and the outlet. Here, parallel means that in each case at least one air inlet duct leads (from a common air inlet opening or separate air inlet openings) to each of the medicament chambers and in each case at least one outlet duct leads out of each medicament chamber into the outlet formed as a mouthpiece or nose nozzle. When the medicament chambers are arranged in series, the air inlet duct extends as far as a first medicament chamber, from there a further duct extends to the next medicament chamber, and the outlet duct extends from, the last medicament chamber to the outlet opening. In each of the medicament chambers there can be a dose of powder, wherein these can be different active agents which only come into contact with each other on use. Thus, although such a powder inhaler in principle contains more than one dose of powder, this powder inhaler should nevertheless be understood according to the invention as being a "single-dose" powder inhaler since this plurality of doses of powder are inhaled in a combined manner in a single use, after which the powder inhaler can no longer be used.

The plastic which is used to produce a powder inhaler according to the invention, which is designed as a disposable item, can preferably be a biodegradable plastic.

Each powder inhaler according to the invention can be at least partially provided with an antiseptic or antibacterial and/or antimicrobial coating. Thus, particularly the air inlet duct, medicament chamber and air outlet duct can be coated in order that no germs are inhaled when the inhalation device is used. However, on account of the easier application, it is also possible for the entire inhalation device to be coated. An example of such a coating is Perlazid® from Rilit, Endingen. Alternatively, an antiseptic or antibacterial and/or antimicrobial plastic can be used to produce the inhalation device.

A powder inhaler according to the invention can also be marketed for example in outer packaging, which ensures that the powder inhaler is clean or sterile and thus ready for immediate use. Alternatively, it may also be conceivable for the covering element to have an overlap at its ends, by way of which the outlet (optionally also the air inlet) can be closed in the manner of a yogurt cup lid. The overlap can then be pulled off from the opening(s) for example by means of a formed tab. In order to prevent the film from then also being able to be pulled off the housing part, a predetermined breaking point, for example a perforation, can be provided at the connecting point of the overlap.

Furthermore, the plastic used to produce a powder inhaler according to the invention can have a marker for the identifiability thereof, in order for it to be possible to identify counterfeits, which do not contain the marker.

Figure 16:
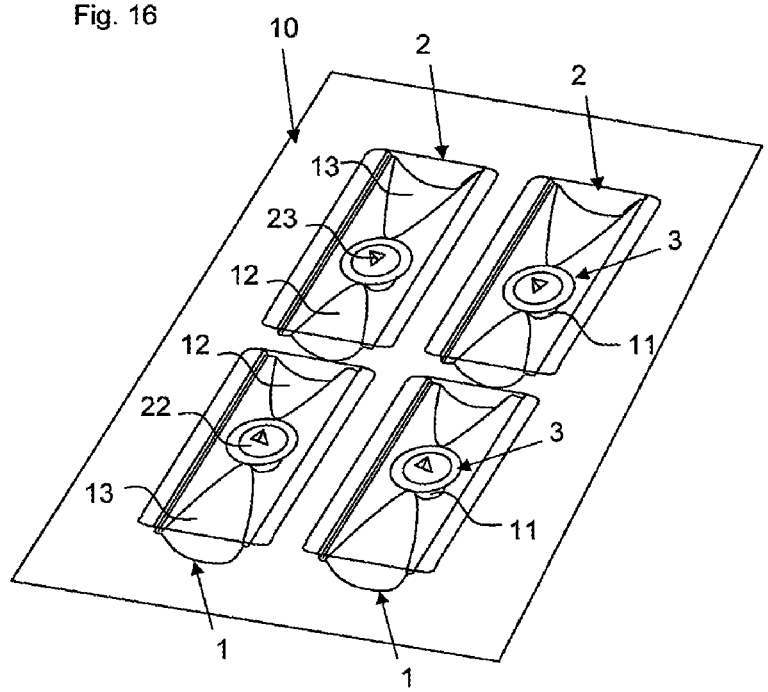
FIG. 16 shows a perspective view of a thermoforming film with four formed housing parts, to which covering elements are attached, before the powder inhalers are cut out.

FIG. 16 reveals a plastic thermoforming film 10 in which four housing parts 1, each with an inlet and outlet duct 12, 13 and a medicament chamber 11, are formed. For greater clarity, not all of the elements of the housing parts have been provided with reference signs. The medicament chambers 11 of the housing parts 1 are filled and closed with a closure tab 30 of a film element 3. It can furthermore be seen that an extensive cover element 2 is attached to each housing part 1, said cover element 2 having a pressure element 22 with a piercing element 23 opposite the medicament chamber 11.

In order to complete the respective powder inhalers, all that is now necessary is for the corresponding filled blister structures to be separated.

In contrast to conventional powder inhalers, the dose of powder is thus not provided in a capsule or a blister which has to be inserted into an inhaler housing before the powder can be inhaled. A powder inhaler according to the invention is formed so to speak by the blister itself, which contains the powder to be inhaled. The insertion of a powder-containing capsule into an inhaler housing can thus be dispensed with.

Figure 17:
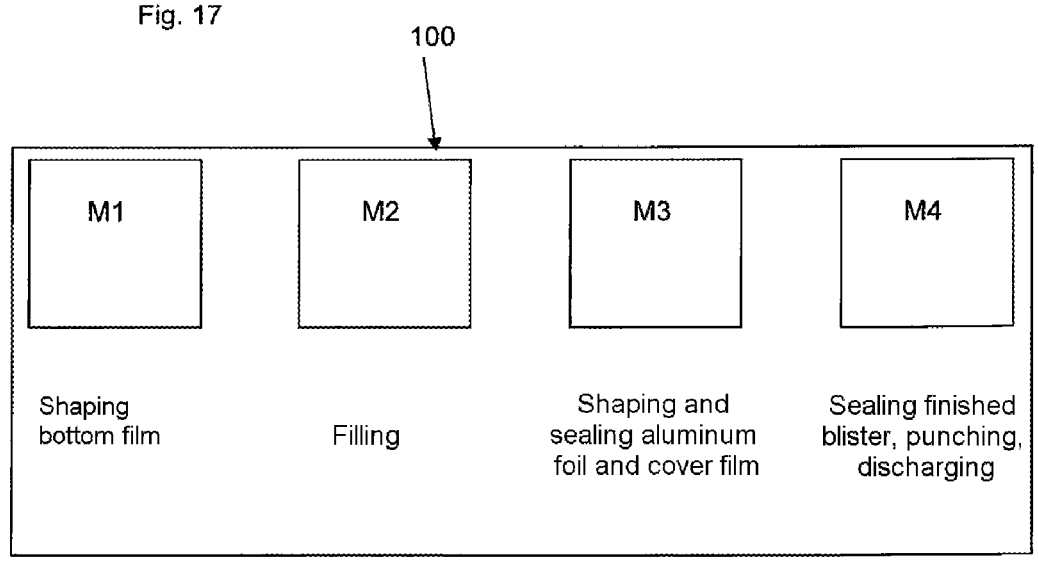
FIG. 17 shows a schematic illustration of a manufacturing device for producing powder inhalers according to the invention.

FIG. 17 summarizes the modules of an exemplary manufacturing device 100 for powder inhalers according to the invention. Of course, other manufacturing devices for carrying out the method steps according to the invention are likewise conceivable. In the first module M1, the shaping of the housing part 1 takes place. In an exemplary method variant, for a continuous process, the thermoforming film can be spliced there from rolled product to form an endless film, prior to preheating and onward transport to the shaping station. As an alternative thereto, semicontinuous or discontinuous processes are also conceivable, in which for example the splicing can be dispensed with. The second module M2 is the filling station, in which the formed medicament chambers are filled with a predetermined type or mixture and quantity of powder. If appropriate, it is also possible for powder compositions and doses that are tailored to a particular patient to be filled in. In the third module M3, the medicament chambers are sealed by a closure film—or closed with the plug elements—and the cover elements are attached in a continuous process. In the case of shaped cover elements, these can likewise be shaped from thermoforming film, in a manner corresponding to the housing parts, in module 1 prior to preheating, placed on the thermoforming film with the housing parts and sealed. In the final module M4, a further sealing station can follow before the powder inhalers made of the thermoforming films are separated, preferably punched, and are discharged as finished blisters.

LIST OF REFERENCE SIGNS

1; 1a Housing part; flat, planar face of housing part 1
10 Thermoforming film
11 Medicament chamber
11a, 11b Subchamber, partition wall
12, 120 Air inlet duct, portion adjacent to the medicament chamber
12' Air inlet opening
13, 130 Outlet duct, portion adjacent to the medicament chamber
13' Outlet opening
14 Nosepiece
15, 16, 17 Air-turbulence-inducing, deflecting, guiding structures
17' Anchoring device
18 Blocking duct
2 Covering element
21 Fold
22 Pressure element
23 Piercing element
3 Film element
30 Closure tab
31 Tape portion
32 Pull-off tab
4 Plug element
40 Plug portion
41 Tape portion
42 Pull-off tab
5 Pull tape
50 End portion
51 Tape portion
52 Pull tab
100 Manufacturing device
Z Traction force
D Pressure
K Points

What is claimed is:

1. A single-dose powder inhaler comprising:
an inhaler housing comprised of a housing part (1), in which a medicament chamber (11) having a dose of a pulverulent medicament is formed, and further comprised of a flat, planar covering element (2) without depressions and projections, wherein the inhaler housing has an outlet opening (13') and an outlet duct (13) which extends from the medicament chamber (11) to the outlet opening (13'), wherein
the housing part (1) has a flat, planar face facing the flat, planar covering element (2), wherein the flat, planar covering element (2) and the flat, planar face are joined to each other to form the inhaler housing, wherein
the outlet duct (13) is a depression formed in the housing part (1) relative to a plane of the flat, planar face and extending away from the flat, planar covering element (2) and the medicament chamber (11) consists of a depression exclusively formed in the housing part (1) relative to the plane of the flat planar face and extending away from the flat, planar covering element (2),
and wherein the housing part (1) comprises
an air inlet opening (12') on a side of the medicament chamber (11) remote from the outlet opening (13'), and
an inlet duct (12), formed as a depression in the housing part (1) relative to the plane of the flat, planar face and extending away from the flat, planar covering element (2), wherein the inlet duct (12) extends from the air inlet opening (12') toward the medicament chamber (11), wherein the outlet duct (13), the medicament chamber (11), and the inlet duct (12) define an axis, wherein air-guiding, turbulence-inducing and/or deflecting structures (15, 16, 17) are formed in the air inlet duct (12), in the medicament chamber (11) and in the outlet duct (13), and
the inlet duct (12) narrows from the air inlet opening (12') toward the medicament chamber (11) in two directions perpendicular to said axis and the outlet duct (13) widens from the medicament chamber (11) in the direction of the outlet opening (13') in two directions perpendicular to said axis;
wherein a closure tab (30) closes off the medicament chamber (11) relative to a space in the housing part (1), wherein the space is arranged between the medicament chamber (11) and the flat, planar covering element (2) and connects the air inlet duct (12) and the outlet duct (13) to each other.

2. The single-dose powder inhaler as claimed in claim 1, wherein
the housing part (1) is an injection-molded plastics part or is shaped or thermoformed from a pharmaceutically compliant plastic film, wherein the flat, planar covering element (2)
is formed in an extensive and planar manner and bounds the inlet duct (12) and the outlet duct (13), and consists of a plastic film, aluminum foil or composite film,
and/or at least one of the housing part (1) and the flat, planar covering element (2) is transparent.

3. The single-dose powder inhaler as claimed in claim 1, wherein
the outlet opening (13') is formed as a mouthpipe or is connected to a nose nozzle (14),
and/or
a cross section of the air inlet duct (12) at the medicament chamber (11) is smaller than a cross section of the outlet duct (13) at the medicament chamber (11).

4. The single-dose powder inhaler as claimed in claim 1, wherein
the closure tab (30) that closes off the medicament chamber (11) is a part of a film element (3).

5. The single-dose powder inhaler as claimed in claim 4, wherein
the film element (3) has at least one pull-off tab (32) which is arranged opposite the closure tab (30) that closes off the medicament chamber (11) and extends out of the air inlet opening or outlet opening (12', 13') of the air inlet duct or outlet duct (12, 13).

6. The single-dose powder inhaler as claimed in claim 1, wherein
the housing part (1) and the flat, planar covering element (2) are comprised of a plastic that
is biodegradable, and/or
contains a marker.

7. The single-dose powder inhaler as claimed in claim 1, wherein
the housing part (1) and the flat, planar covering element (2) are comprised of a plastic that is an antiseptic and/or antimicrobial plastic,
or
at least the air inlet duct (12), the medicament chamber (11) and the outlet duct (13) are provided with an antiseptic and/or antimicrobial coating.

8. The single-dose powder inhaler (1) as claimed in claim 1, wherein
the medicament chamber (11) is subdivided into at least two subchambers (11*a*) by at least one partition wall (11*b*), or
two or more of said medicament chamber (11) are formed in the housing part (1), which are arranged in parallel alongside one another with an air inlet duct (12) and an outlet duct (13) or are arranged in series with one another, wherein the air inlet duct (12) leads to a first one of the two or more medicament chambers (11) and the outlet duct (13) extends from a last one of the two or more medicament chambers (11) and the two or more medicament chambers (11) are connected to each other by a further duct.

9. The single-dose powder inhaler (1) as claimed in claim 8, wherein
the flat, planar covering element (2) comprises a pressure element (22) provided with at least one piercing element (23) for each subchamber (11*a*) formed in the housing part (1), or
the flat, planar covering element (2) comprises a resilient pressure element (22) provided with at least one piercing element (23) for each medicament chamber (11) formed in the housing part (1).

10. A method for producing a single-dose powder inhaler as claimed in claim 1,
comprising the steps of
producing the housing part (1) from plastic by injection-molding or by thermoforming a plastic film,
filling the medicament chamber (11) with a dose of a pulverulent medicament,
closing the medicament chamber (11) with a film element (3) and
cutting out the flat, planar covering element (2) or producing the flat, planar covering element (2) from plastic by injection-molding or by thermoforming a plastic film,
attaching the flat, planar covering element (2) to the housing part (1), wherein the method is carried out in a single device.

11. A single-dose powder inhaler comprising:
an inhaler housing comprised of a housing part (1), in which a medicament chamber (11) having a dose of a pulverulent medicament is formed, and further comprised of a flat, planar covering element (2), wherein the inhaler housing has an outlet opening (13') and an outlet duct (13) which extends from the medicament chamber (11) to the outlet opening (131 wherein
the housing part (1) has a flat, planar face facing the flat, planar covering element (2), wherein the flat, planar covering element (2) and the flat, planar face are joined to each other to form the inhaler housing, wherein
the outlet duct (13) is a depression formed in the housing part (1) relative to a plane of the flat, planar face and extending away from the flat, planar covering element (2) and the medicament chamber (11) consists of a depression exclusively formed in the housing part (1) relative to the plane of the flat planar face and extending away from the flat, planar covering element (2),
and wherein the housing part (1) comprises
an air inlet opening (12') on a side of the medicament chamber (11) remote from the outlet opening (13'), and
an inlet duct (12), formed as a depression in the housing part (1) relative to the plane of the flat, planar face and extending away from the flat, planar covering element (2), wherein the inlet duct (12) extends from the air inlet opening (12') to the medicament chamber (11), wherein the outlet duct (13), the medicament chamber (11), and the inlet duct (12) define an axis,
wherein air-guiding, turbulence-inducing and/or deflecting structures (15, 16, 17) are formed in the air inlet duct (12), in the medicament chamber (11) and in the outlet duct (13), and
the inlet duct (12) narrows from the air inlet opening (12') to the medicament chamber (11) in two directions perpendicular to said axis and the outlet duct (13) widens from the medicament chamber (11) in the direction of the outlet opening (13') in two directions perpendicular to said axis,
wherein
a first blocking duct (18) is formed in the housing part (1) on a first side of the medicament chamber (11) and a second blocking duct (18) is formed in the housing part (1) on a second side of the medicament chamber (11) at right angles to the air inlet duct (12) and the outlet duct (13), respectively, wherein a first correspondingly formed fold (21) of the covering element (2) and a second correspondingly formed fold (21) of the covering element (2) are received in said first and second blocking ducts (18), respectively, so as to sealingly close the air inlet duct (12) and the outlet duct (13), wherein the powder inhaler has a lifting element enabling the first and second folds (21) to be lifted out of the first and second blocking ducts (18), respectively.

12. The single-dose powder inhaler as claimed in claim 11, wherein the lifting element is at least one predetermined and marked pressure, bending or pulling point (D, Z) on the inhaler housing, or is a pull tape (5) which extends through the air inlet duct (12) and/or the outlet duct (13) and transversely through the first and second blocking ducts (18) between the first and second folds (21) and the housing part (1), and wherein the pull tape (5) has a grip portion (52) at a first end of the pull tape (5) and wherein a second end (50) of the pull tape (5) is anchored to an anchoring structure (17') of the inhaler housing, or is a structure arranged loosely in the medicament chamber.

13. A method for producing a single-dose powder inhaler as claimed in claim 11, comprising the steps of producing the housing part (1) from plastic by injection-molding or by thermoforming a plastic film, filling the medicament chamber (11) with a dose of a pulverulent medicament, closing the medicament chamber (11) by a fold (21) of the flat, planar covering element (2), received in a blocking duct (18) of the housing part (1), and cutting out the flat, planar covering element (2) or producing the flat, planar covering element (2) from plastic by injection-molding or by thermoforming a plastic film, attaching the flat, planar covering element (2) to the housing part (1), wherein the method is carried out in a single device.

14. A single-dose powder inhaler comprising:

an inhaler housing comprised of a housing part (1), in which a medicament chamber (11) having a dose of a pulverulent medicament is formed, and further comprised of a flat, planar covering element (2) without depressions and projections, wherein the inhaler housing has an outlet opening (13') and an outlet duct (13) which extends from the medicament chamber (11) to the outlet opening (13'), wherein the housing part (1) has a flat, planar face facing the flat, planar covering element (2), wherein the flat, planar covering element (2) and the flat, planar face are joined to each other to form the inhaler housing, wherein the outlet duct (13) is a depression formed in the housing part (1) relative to a plane of the flat, planar face and extending away from the flat, planar covering element (2) and the medicament chamber (11) consists of a depression exclusively formed in the housing part (1) relative to the plane of the flat planar face and extending away from the flat, planar covering element (2), and wherein the housing part (1) comprises an air inlet opening (12') on a side of the medicament chamber (11) remote from the outlet opening (13'), and an inlet duct (12), formed as a depression in the housing part (1) relative to the plane of the flat, planar face and extending away from the flat, planar covering element (2), wherein the inlet duct (12) extends from the air inlet opening (12') to the medicament chamber (11), wherein the outlet duct (13), the medicament chamber (11), and the inlet duct (12) define an axis, wherein air-guiding, turbulence-inducing and/or deflecting structures (15, 16, 17) are formed in the air inlet duct (12), in the medicament chamber (11) and in the outlet duct (13), and the inlet duct (12) narrows from the air inlet opening (12') to the medicament chamber (11) in two directions perpendicular to said axis and the outlet duct (13) widens from the medicament chamber (11) in the direction of the outlet opening (13') in two directions perpendicular to said axis, wherein the medicament chamber (11) is closed by two plug elements (4) positioned opposite each other in relation to the medicament chamber (11), wherein each plug element (4) has a plug portion (40), which is arranged adjacent to the medicament chamber (11) in the air inlet duct (12) or the outlet duct (13), respectively, to close off a flow cross section of the air inlet duct (12) or the outlet duct (13), respectively, wherein each plug element (4) further comprises a pull-off tab (42) which extends out of the air inlet opening (12') or the outlet opening (13'), respectively.

15. A method for producing a single-dose powder inhaler as claimed in claim 14, comprising the steps of producing the housing part (1) from plastic by injection-molding or by thermoforming a plastic film, filling the medicament chamber (11) with a dose of a pulverulent medicament, closing the medicament chamber (11) by two plug elements (4), and cutting out the flat, planar covering element (2) or producing the flat, planar covering element (2) from plastic by injection-molding or by thermoforming a plastic film, attaching the flat, planar covering element (2) to the housing part (1), wherein the method is carried out in a single device.

* * * * *